United States Patent [19]

Simon et al.

[11] Patent Number: 5,064,757
[45] Date of Patent: Nov. 12, 1991

[54] T4 DNA FRAGMENT AS A STABILIZER FOR PROTEINS EXPRESSED BY CLONED DNA

[75] Inventors: Lee D. Simon, Philadelphia, Pa.; Rose B. Fay, Piscataway, N.J.

[73] Assignee: Rutgers Research and Educational Foundation, New Brunswick, N.J.

[21] Appl. No.: 512,529

[22] Filed: Apr. 18, 1990

Related U.S. Application Data

[63] Continuation of Ser. No. 178,861, Apr. 6, 1988, abandoned, which is a continuation of Ser. No. 17,016, Feb. 24, 1987, abandoned, which is a continuation of Ser. No. 293,614, Aug. 17, 1981, abandoned.

[51] Int. Cl.$^5$ ............................................. C12N 15/00
[52] U.S. Cl. .............................. 435/71.2; 435/172.1; 435/172.2; 435/320.1; 435/252.3; 435/252.33; 435/252.34; 536/27; 536/28; 536/29; 935/6; 935/33; 935/47; 935/48; 935/49
[58] Field of Search ................. 435/71.2, 172.1, 172.2, 435/317, 320.1, 252.3; 935/6, 33, 47–49; 536/27–29

[56] References Cited

U.S. PATENT DOCUMENTS 4,237,224  12/1980  Cohen et al. .................... 435/172
4,336,336   6/1982  Silhavy et al. .................. 435/172

OTHER PUBLICATIONS

Lee D. Simon & Kathleen Tomczak, "Bacteriophages Inhibit Degradation of Abnormal Proteins in *E. coli*", Nature, vol. 275, No. 5679, pp. 424–428, Oct. 5, 1978.
Lee D. Simon et al., "Hyperdegradation of Proteins in *Escherichia coli* rho Mutants", Proc. Natl. Acad. Sci. U.S.A., vol. 76, No. 4, pp. 1623–1627, Apr. 1979.
Humayun et al., The Single-Stranded DNA Phages (Denhardt, Ed.), Cold Spring Harbor, 1978, pp. 477–481.
Wais et al., Growth and Transformation of Phage T4 in Escherichia coli B/4, Salmonella, Aerobacter, Proteus, and Serratia, 1969, Virology 39, pp. 153–161.
Skorupski et al., A Bacteriophage T4 Gene Which Functions to Inhibit Escherichia coli Lon Protease, 1988, Journal of Bacteriology, pp. 3016–3024.
Richard J. Roberts, Recombinant DNA, Methods in Enzymology, vol. 68, 1979, pp. 27–35, 40.
Rupprecht et al., Conservation of capR (lon) DNA of Escherichia coli K-12 Between Distantly Related Species, 1983, Journal of Bacteriology, vol. 155, No. 2, pp. 910–914.
Benjamin Lewin, Plasmids and Phages, 1977, Gene Expression, p. 536.

Primary Examiner—Christine Nucker
Attorney, Agent, or Firm—John R. Wetherell, Jr.

[57] ABSTRACT

A DNA fragment isolated from the DNA of T-even bacteriophage which suppresses the degradation of abnormal proteins in bacterial cells is disclosed. The DNA fragment can be isolated by treating the DNA of T-even bacteriophage with a restriction enzyme to cleave the DNA into fragments, at least one of said fragments consisting essentially of a sequence of nucleotide bases which code for protein that functions to suppress degradation of abnormal proteins in bacterial cells, inserting the DNA fragments into cloning vehicles, such as plasmids, to produce hybrid cloning vehicles, transforming bacterial cells by introducing the hybrid cloning vehicles therein, and selecting the transformants which exhibit suppressed protein degradation mechanisms. The DNA fragment can then be isolated from the selected transformants. The stabilizing DNA fragment can be introduced into bacterial host cells to increase the yield of foreign proteins expressed by cloned DNA.

12 Claims, 1 Drawing Sheet ic
T4 DNA FRAGMENT AS A STABILIZER FOR PROTEINS EXPRESSED BY CLONED DNA This is a continuation of application Ser. No. 178,861 filed Apr. 6, 1988, which in turn, is a continuation of application Ser. No. 017,016 filed Feb. 24, 1987, abandoned, which, in turn, is a continuation of Ser. No. 293,614 filed Aug. 17, 1981, abandoned.

BACKGROUND OF THE INVENTION

The work described herein was supported, in part, by Grant PHS GM 27314 from the U.S. Public Health Service, Institute of General Medical Sciences.

This invention relates to the field of recombinant DNA. In one of its aspects, this invention relates to a DNA fragment which inhibits degradation of abnormal proteins in bacterial cells. In another aspect, this invention relates to a method of isolating this stabilizing DNA fragment from T-even phage particles. In another aspect, this invention relates to a plasmid containing the stabilizing DNA fragment. In yet another aspect, this invention relates to a method of amplifying foreign proteins encoded by cloned DNA by including the stabilizing DNA fragment into the genetic machinery of bacterial host cells.

Most living cells possess efficient systems for recognizing and eliminating abnormal proteins. As used herein, the term "abnormal proteins" refers to proteins with abnormal conformations, protein fragments, polypeptide sequences containing amino acid analogues, missense mutant proteins, nonsense protein fragments, proteins encoded by cloned DNA, and other polypeptides not ordinarily present in healthy, viable cells. In $E.$ $coli$ cells, for example, the half-lives of protein fragments and protein with abnormal conformations are much shorter than the half-lives of normal proteins. About 3% of normal proteins turns over each hour in $E.$ $coli$ cells. Abnormal proteins, however, are so short-lived that they are found in much lower quantities than normal proteins or fail to accumulate to detectable levels.

Little is known about the mechanism by which living cells detect and degrade abnormal proteins. Some information is available about this system in $E.$ $coli$ cells. See, for example, Simon et al., $Nature$, 275, 424 (1978). It is known that the degradation of abnormal proteins in $E.$ $coli$ cells is ATP-dependent. If cellular ATP levels are substantially reduced, the turnover of abnormal proteins and protein fragments is also reduced. It is also believed that the ATP-dependent degradative mechanism is bound to the $E.$ $coli$ cell membrane. However, the identities and functions of the enzymes responsible for recognizing and degrading abnormal proteins remain obscure in $E.$ $coli$ and in other bacterial cells.

The degradation systems possessed by living cells present a major obstacle to the manufacture of useful proteins by means of recombinant DNA or molecular cloning procedures. By these procedures, the genes which code for eukaryotic proteins are introduced into host cells, such as bacterial cells, which then express the foreign genes as the eukaryotic proteins. The recombinant DNA procedures involve isolating the relevant genes, inserting them into suitable cloning vehicles, such as bacterial plasmids or viruses, and transforming host cells by introducing the hybrid cloning vehicles into the cells. The transformed cells which contain the relevant genes are then selected from all the other cells and are grown in cultures By such techniques, bacterial cells have been induced thus far to manufacture human growth hormone, human insulin, human interferon, etc. However, the bacterial cells apparently recognize these products as abnormal proteins, and under most circumstances, degrade them. Thus, the ability of living cells to detect and degrade abnormal proteins may severely limit the yields of useful proteins obtained from cloned cells.

To increase such yields, it would be highly desirable to provide a method for inhibiting or suppressing the degradation mechanism in cells carrying cloned genes. Such a method, when combined with already known recombinant DNA methods, would provide a highly efficient means for producing useful proteins.

It has previously been reported that the bacteriophage known as T4 influences the degradation function in $E.$ $coli$ cells. Simon et al., in $Nature$, supra, reported that T4 infection of $E.$ $coli$ cells inhibits degradation of abnormal polypeptide sequences but does not affect the turnover rate of normal bacterial proteins. In the studies reported therein, it was found that adsorption of T4 particles to the $E.$ $coli$ surface and injection of T4 DNA were not by themselves sufficient to alter protein turnover. It was found that inhibition of degradation requires the synthesis of early T4 proteins. It was also reported therein that other phages, such as T5 and T7, also inhibit degradation in $E.$ $coli$ cells but not as to great an extent as does T4 phage. However, infecting $E.$ $coli$ cells with T4, T5 or T7, phage particles is fatal to the host cells, and this method is unsuitable for amplifying proteins expressed by cloned DNA.

In order to maximize the yields of eukaryotic proteins produced by recombinant DNA techniques, it would be highly desirable to excise from T4 phage particles the gene(s) responsible for inhibiting the degradation mechanism and to insert the same gene(s) into bacterial host cells. In this manner, the degradation mechanism of cells carrying cloned DNA can be turned off without killing the cells as by infection with T4 phage particles.

It would thus be desirable to isolate a DNA fragment from T4 phage particles which will inhibit the degradation of abnormal proteins in bacterial host cells.

It would also be desirable to produce a cloning vehicle, such as a bacterial plasmid, which contains the stabilizing T4 DNA fragment.

It would also be desirable to transform bacterial cells by introducing the stabilizing T4 DNA fragment.

It would further be desirable to produce transformants which contain the genes for producing eukaryotic proteins as well as the stabilizing T4 DNA fragment.

SUMMARY OF THE INVENTION

These and other objects are accomplished by means of the present invention which comprises, in one of its aspects, a DNA fragment isolated from a T-even bacteriophage, consisting essentially of a sequence of nucleotide base pairs which codes for protein that functions to suppress the mechanism that degrades abnormal proteins in bacterial cells.

In another of its aspects, the present invention comprises a method of isolating the stabilizing DNA fragment comprising treating the DNA of a T-even bacteriophage with a restriction enzyme to cleave the DNA into fragments, at least one of said fragments coding for protein that causes the suppression of degradation of abnormal proteins in bacterial cells, inserting said DNA fragments into cloning vehicles, such as bacterial plasmids, to produce hybrid cloning vehicles, transforming bacterial cells by introducing said hybrid cloning vehicles therein, and selecting the transformants which exhibit suppressed degradation of abnormal proteins. As used herein, the term "hybrid cloning vehicle" refers broadly to a cloning vehicle, such as a bacterial plasmid, containing a T-even DNA insert.

In another of its aspects, this invention comprises a method for increasing the yield of proteins expressed by cloned DNA in a bacterial cell, comprising inserting the DNA fragment into a cloning vehicle, such as a bacterial plasmid, to produce a hybrid cloning vehicle, and transforming the bacterial cell containing the cloned DNA by introducing said hybrid cloning vehicle into said bacterial cell.

In another of its aspects, this invention comprises a hybrid cloning vehicle, such as a plasmid, containing the stabilizing DNA fragment.

In another of its aspects, this invention comprises a bacterial cell containing the specific DNA fragment that functions to inhibit protein degradation.

DETAILED DESCRIPTION OF THE INVENTION

Figure 1:
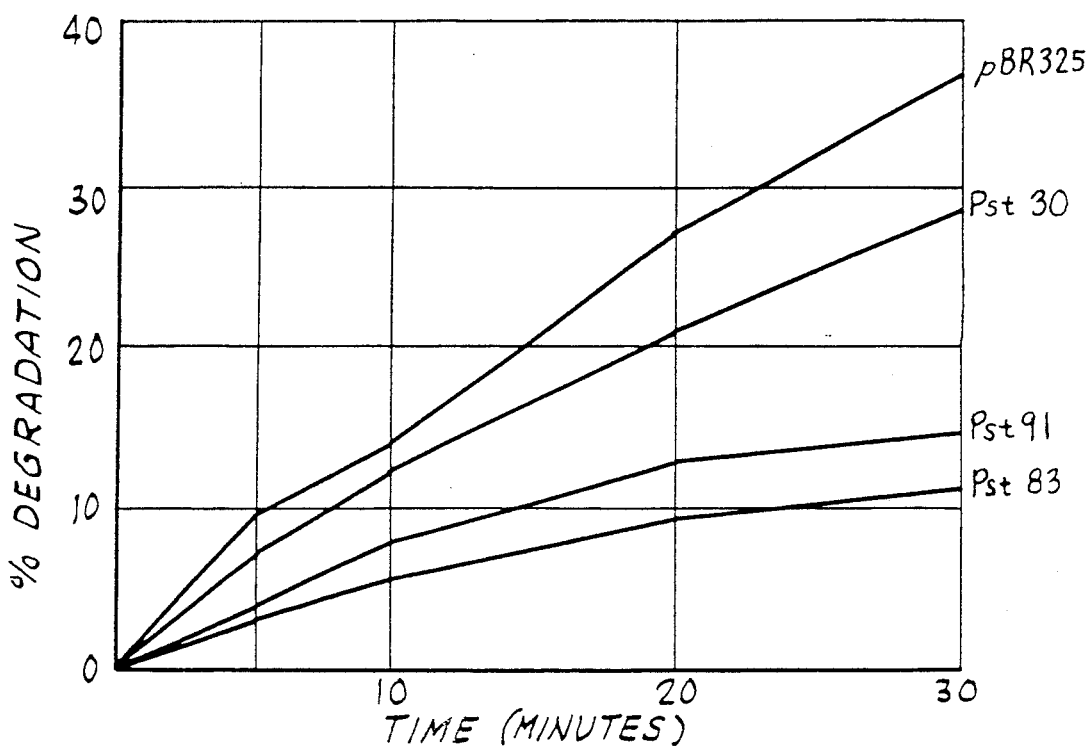

The bacteriophage T4 together with the bacteriophages T2 and T6 form a family of bacteriophages known as T-even phages. The T-even phages are almost identical in structure, composition and properties. Thus, one of ordinary skill in the art would conclude that all members of the T-even bacteriophage family contain genes which suppress degradation.

The genetic map of T4 phage is known to be circular and to contain about 150 genes. About 40 different T4 gene products, each coded by a specific T4 gene, interact to produce the coat proteins which form the mature virus particle. It is not known how many genes are responsible for suppressing degradation of abnormal proteins in bacterial hosts. Nor is it known which proteins are expressed by these genes. However, as a result of the practices of the present invention, it has been learned that a DNA fragment which codes for protein that functions to suppress degradation of abnormal proteins in bacterial cells originates from the vicinity of gene 49 of the T4 genetic map.

Wais, et al., in *Virology*, 39, 153 (1969), have reported that T4 phage is able to replicate when injected into a variety of bacteria, including *E. coli* strain B/4, Salmonella, Aerobacter, Proteus, and Serratia. Thus, the genetic machinery of T4 is unimpaired and is able to function essentially normally when inserted in a wide variety of host cells.

The genetic nucleic acid present in the core of the T4 phage particle is double-stranded DNA. T4 DNA comprises about $3.6 \times 10^5$ base pairs (MW ca. $1.2 \times 10^8$). There are twice as many A-T base pairs as G-C base pairs. T4 DNA is unusual in that it contains the base 5-OH- methylcytosine in place of the more usual cytosine. Moreover, one or more glucose residues are attached to some of the $5\text{-CH}_2\text{OH}$ cytosine groups in the T4 DNA. 5-OH-methylcytosine, like cytosine, forms base pairs with guanine. The presence of 5-OH-methylcytosine and its glucose derivatives in place of cytosine has no bearing on the genetic properties of T4 phage. The biological significance of the unusual base has not yet been clearly established although it is believed that its function is to protect T4 DNA from a phage specific enzyme which destroys unmodified DNA.

In accordance with the present invention, a process is disclosed for isolating a specific DNA fragment from T-even phage particles which will suppress degradation of abnormal proteins, such as foreign proteins encoded by cloned DNA, in bacterial cells. The process begins with the extraction of DNA from the capsids of T-even phage particles.

T-even DNA may be extracted from the capsids of the T-even particles by well known methods. Both chemical or mechanical methods are known to remove the DNA from the T-even particles although chemical methods are preferred since they are less likely to damage the DNA. For purposes of the present invention, it is preferable that the DNA come from T-even mutants in which the DNA is cytosine-containing and nonglucosylated. This form of DNA is preferred since most restriction enzymes will not act on wild-type T4 DNA. Furthermore, wild-type T4 DNA may not be transcribed in host cells as well as cytosine-containing, nonglucosylated DNA.

After the DNA has been extracted from the T-even phage particles, the DNA is digested with a suitable restriction endonuclease. The restriction enzyme scans the DNA strand and cleaves it into fragments whenever a particular short sequence of nucleotides is encountered. Each restriction enzyme therefore cleaves the T-even DNA into a characteristic set of fragments which can be separated, if desired, by well known methods such as gel electrophoresis. It is essential that the restriction enzyme not cleave the DNA within the gene(s) responsible for suppressing degradation of abnormal proteins. A variety of restriction enzymes have been found suitable for the practice of the present invention, including such well known endonucleases as Pst I and Eco RI.

To isolate the specific T-even DNA fragment containing the stablizing gene(s), the fragments are inserted into suitable cloning vehicles to produce hybrid cloning vehicles. Both viruses and plasmids are suitable cloning vehicles; however, bacterial plasmids carrying genes which serve as recognition markers, such as antibiotic resistance, may be preferred. For example, the readily available plasmid pBR 325, which confers resistance to ampicillin, chloramphenicol, and tetracycline, or the readily available plasmid pBR 322, which confers resistance to ampicillin and tetracycline, are suitable cloning vehicles for the present invention.

The T-even DNA fragments can be inserted into the cloning vehicles, such as the bacterial plasmids, by a variety of enzymatic techniques. When the T-even DNA has been cleaved with a restriction enzyme leaving "sticky ends", the same restriction enzyme can be used to cleave open the appropriate bacterial plasmid. The bacterial plasmid will then have matching sticky ends and the DNA fragments can be directly annealed to the bacterial plasmids. However, if the restriction enzyme leaves blunt ends, the enzyme terminal transferase can be used to provide a short sequence of identical bases, such as four cytosines, to the DNA fragments. The fragments can then be annealed to the plasmid DNA to which a complementary sequence of bases (four guanines) have been added.

The hybrid cloning vehicles are next inserted into bacterial host cells. Treatment with a dilute solution of calcium chloride is known to render the cell walls permeable to plasmids. *E. coli* cells have been found to be suitable host cells for expressing the stabilizing DNA fragment although the method of the present invention is not confined to these cells. *E. coli* is classified as a gram-negative species of bacteria. Other gram-negative bacteria such as Pseudomonas, Aerobacter, etc., are also suitable hosts for expressing the stabilizing function of the DNA fragment. With suitable modification in the Shine-Dalgar sequence, gram-positive bacteria, such as *Bacillus subtilis*, will also serve as suitable hosts for the stabilizing DNA fragment. The modification techniques are conventionally known in the art.

To select the host cells which have been transformed by the hybrid cloning vehicles, bacteria are grown first in a non-selective medium and then in a selective medium. For example, the restriction enzyme Pst I cuts the plasmid of pBR 325 in the midst of the gene which confers ampicillin resistance, but leaves the genes which confer chloramphenicol and tetracycline resistance intact. Thus, one can select the transformed cells containing inserts in the Pst I site of pBR 325 by screening for resistance to chloramphenicol and tetracycline and sensitivity to ampicillin.

To isolate those transformants containing the stabilizing DNA fragment, the transformants are screened for those which exhibit suppressed degradation of abnormal proteins. A test based upon the ability of temperature sensitive phage mutants to propagate in the transformants has been found suitable for this purpose. At appropriate temperatures, the phage mutant will only grow in host cells having defective mechanisms for degradation of abnormal proteins. For example, the phage mutant known as λOts is a λ phage with a defect in gene O. The λO protein is vital to the survival of the virus. Wild-type phage is able to propagate in *E. coli* at 30° and at 39° C. λOts, however, is unable to propagate at 39° C. unless the degradation mechanism of the *E. coli* cells is impaired (see Simon et al., *Proc. Nat. Acad. Sci. U.S.A.*, 76, 1623 (1979)). Thus, the transformants containing the desired T-even DNA fragment can be selected by their ability to propagate the λOts phage mutants at 30° C. and at 39° C. If desired, these transformants can be tested further for their ability to degrade abnormal proteins and protein fragments by methods described in Simon et al., *Nature, supra*.

In this manner transformants are isolated having an impaired degradation mechanism. The transformants contain a hybrid cloning vehicle such as a plasmid, in which a DNA fragment from T-even phage has been inserted. This DNA fragment is functional in bacteria, and contains the genetic information required to inhibit abnormal protein degradation.

The plasmid can be removed from the selected transformants and introduced into other host cells where it will inhibit degradation in the new host cells. The new host cells are not confined to *E. coli* but may be any of a wide variety of bacterial cells, including Pseudomonas, Aerobacter, etc., and, with suitable modification of the Shine-Dalgar sequence, *Bacillus subtilis*, etc. The new host cells may additionally carry an appropriate recombinant plasmid for producing eukaryotic proteins. The presence of the stabilizing DNA fragment will increase dramatically the yields of the eukaryotic proteins.

Alternatively, the T-even DNA fragment may be excised from the hybrid plasmid by treatment with a restriction enzyme, for example, Pst I. The DNA fragment may then be inserted into a cloning vehicle, such as a plasmid, already carrying a gene for producing a eukaryotic protein. When the new recombinant plasmid is introduced into a host cell, the yields of the eukaryotic protein will be greatly increased.

After the stabilizing DNA fragment has been isolated, it may be subjected to further analysis and study. For example, the DNA fragment can be sequenced by laborious but well known techniques. The DNA fragment may also be subcloned to find the smallest DNA fragment which would inhibit degradation in bacterial cells. Subcloning can be accomplished by digesting the stabilizing DNA fragment with a variety of restriction enzymes in order to cut it into smaller fragments. Each of these pieces can then be inserted into a plasmid and then cloned in a bacterial host. The hosts can then be screened for impaired degradation. In this manner, the smallest DNA fragment can be isolated which codes for protein that suppresses degradation of abnormal proteins in bacteria.

The practices of the present invention may be further illustrated by the following examples.

EXAMPLE 1

For purposes of testing the practices of the present invention, DNA was extracted by well known methods from T4 mutants having the following mutations: alc−, den A−, den B−, 42−, 56−. These mutations result in T4 particles having cytosine-containing, non-glycosylated DNA.

The DNA from the T4 mutants was cleaved with the restriction endonuclease Pst I. This restriction enzyme recognizes the nucleotide sequence CTGCA ↓ G and cuts the T4 DNA between A and G wherever this sequence appears. Digestion of T4 DNA with Pst I produced about 35 DNA fragments of various lengths.

At the same time, the bacterial plasmid known as pBR 325 was also cleaved with Pst I. Pst I cleaved pBR 325 provides chloramphenicol and tetracycline resistance but not ampicillin resistance. The T4 DNA fragments were then directly annealed to the Pst I cleaved pBR 325 plasmids to produce hybrid plasmids.

*E. coli* cells, strain C600 (a K12 strain) were then transformed by mixing with the pBR 325 plasmids in a dilute solution of calcium chloride. The transformed bacteria were grown first in a nonselective medium, and then in a selective medium which screened for chloramphenicol and tetracycline resistance and ampicillin sensitivity. In this way individual transformants which had taken up the hybrid pBR 325 plasmids were isolated and cultured as colonies. Each of the colonies was given a number.

To isolate the *E. coli* transformants which contain the stabilizing DNA fragment, individual transformants were cultured. The cultures were then infected with λOts mutants and incubated as plate assays at 30°, 37° and 39° C. The number of plaques per plate for each culture was counted. The relative efficiency of plaque formation for selected cultures is shown in Table 1.

TABLE 1

| PLASMID | Efficiency of Plaque Format At: | | |
|---|---|---|---|
| | 30° C. | 37° C. | 39° C. |
| pBR 325 | 1 | 0.38 | 0.02 |
| Pst 30 | 1 | 0.78 | 0.78 |
| Pst 83 | 1 | 1.43 | 0.76 |
| Pst 91 | 1 | 1.43 | 1.11 |

In Table 1, the designation pBR 325 indicates host cells containing the plasmid pBR 325. These cells served as a control. The designation Pst 30 indicates host cells containing the plasmid pBR 325 with the T4 DNA insert of colony 30. Similarly Pst 83 and Pst 91 indicate host cells containing the plasmid pBR 325 with the T4 DNA inserts of colonies 83 and 91 respectively.

As can be seen in Table 1, the ability of λ0ts to propagate at 39° C. was drastically reduced in *E. coli* cells having only the pBR 325 control. However, λ0ts was able to propagate well at 39° C. in *E. coli* cells having the T4 DNA inserts of colonies 30, 83 and 91. The ability of λ0ts to propagate at 39° C. was due to the suppressed degradation of abnormal protein in the *E. coli* cells having the T4 DNA inserts of colonies 30, 83 and 91.

EXAMPLE 2

The hybrid plasmids of Example 1 were introduced into *E. coli* cells, strain SG 13062 (a K12 strain). Transformants were examined for their ability to degrade puromycyl protein fragments by the methods described in Simon et al., *Nature, supra*. The results are shown in FIG. 1, wherein the designations are the same as in Example 1.

As can be seen in FIG. 1, *E. coli* cells containing T4 DNA fragments from colonies 83 and 91 show substantially lower levels of degradation than *E. coli* cells containing only the pBR 325 plasmid. Moreover, these *E. coli* cells exhibited no change in the turnover rate of normal proteins.

EXAMPLE 3

Figure 2:
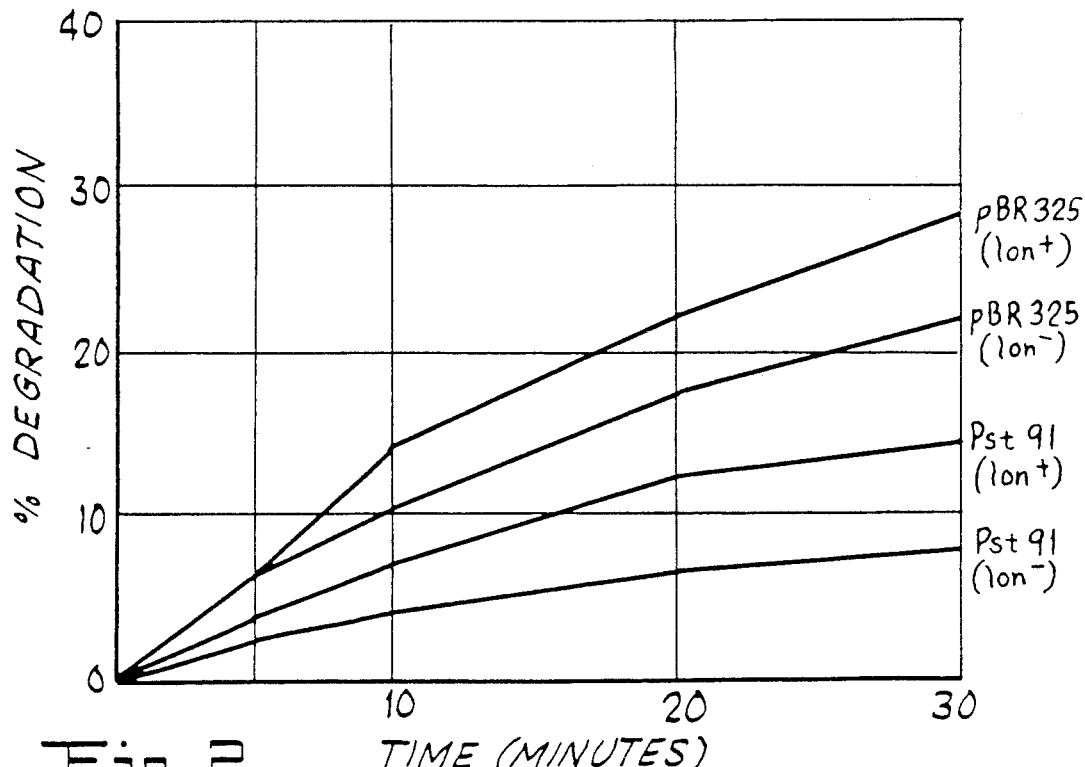

The hybrid plasmid Pst 91 was introduced into *E. coli* cells, strains SG 13062 and SG 13069 (both K12 strains). SG 13062 served in this example as a wild-type *E. coli* strain. SG 13069 is identical to SG 13062 except that SG 13069 carries the mutation designated lon−. This mutation of the *E. coli* genome reduced the efficiency of the degradation mechanism. The *E. coli* transformants were examined for their ability to degrade puromycyl polpeptides. The results are shown in FIG. 2. The results demonstrate that *E. coli* cells having the stabilizing T4 DNA fragment exhibit less degradation of abnormal proteins than *E. coli* lon− mutants. FIG. 2 also shows that degradation is smallest in lon− mutants having the stabilizing T4 DNA fragment.

EXAMPLE 4

*E. coli* cells of the strain designated 294 (a K12 strain) were transformed with plasmid Pst 91 or with pBR 325. The *E. coli* cells had previously been transformed with the plasmid designated PACY184IF. This plasmid contains the gene which codes for human fibroblast interferon. The transformants were cultured and the interferon production was assayed. The results are shown in Table 2.

TABLE 2

| PLASMIDS | INTERFERON (units/ml culture) |
|---|---|
| PACY184IF | 150 |
| PACY184IF + pBR 325 | 150 |
| PACY184IF + Pst 91 | 600 |

Table 2 demonstrates that *E. coli* clones carrying the gene for human interferon and the stabilizing T4 DNA fragment yielded four times as much interferon as clones not having the T4 DNA fragment

EXAMPLE 5

The T4 DNA fragment was excised from Pst 91 with Pst I and inserted into the plasmid designated 177. Plasmid 177 contained the gene coding for human fibroblast interferon. *E. coli* cells, strain 294, were transformed with the new plasmid designated 177-91. The transformants were cultured and the interferon was extracted after freeze-thaw cycles and assayed. The results are shown in Table 3.

TABLE 3

| PLASMID | INTERFERON (units/ml culture) |
|---|---|
| 177 | 150 |
| 177-91 | 600 |

As in Example 4, the *E. coli* clones carrying the gene for human interferon and the stabilizing T4 DNA fragment yielded four times as much interferon as clones not carrying the T4 DNA fragment.

EXAMPLE 6

*E. coli* cells, strain 294 were transformed with the plasmid 177-91 as in Example 5. The transformants were cultured and the interferon was extracted following treatment of the cells with the detergent Triton X100. The interferon was assayed and the results are shown in Table 4.

TABLE 4

| PLASMID | INTERFERON (units/ml culture) |
|---|---|
| 177 | 300 |
| 177-91 | 2400 |

In this case, the host cells having the stabilizing T4 DNA fragment yielded eight times as much interferon as cells without the fragment.

While the invention has been described with reference to specific embodiments, this should not be construed to limit the spirit or the scope of the invention.

What is claimed is:

1. An isolated DNA fragment consisting essentially of the nucleotide sequence found in the vicinity of gene 49 of a T-even bacteriophage, wherein the fragment encodes a protein that inhibits degradation of abnormal proteins in a gram-negative bacteria.

2. The fragment of claim 1, wherein the gram-negative bacteria is selected from the group consisting of members of the genera Escherichia, Salmonella, Shigella, Aerobacter, Proteus, Pseudomonas, and Serratia.

3. The fragment of claim 1, wherein the gram-negative bacteria is *Escherichia coli*.

4. The fragment of claim 1, wherein the bacteriophage is T4.

5. The fragment of claim 1, wherein the fragment is isolated through initial excision using Pst I.

6. A cloning vehicle comprising the DNA fragment of claim 1.

7. The cloning vehicle of claim 6, which is a plasmid.

8. The cloning vehicle of claim 6, which further comprises a DNA sequence encoding a eukaryotic protein.

9. A gram-negative bacteria containing the cloning vehicle of claim 6.

10. The gram-negative bacteria of claim 9, further containing a second cloning vehicle, wherein the second cloning vehicle comprises a DNA sequence which encodes a eukaryotic protein.

11. The gram-negative bacteria of claim 9, wherein the cloning vehicle further comprises a DNA sequence encoding a eukaryotic protein.

12. A method for inhibiting the degradation of abnormal proteins in a gram-negative bacteria which comprises transforming the bacteria with the DNA fragment of claim 1.

* * * * *